United States Patent [19]

Bracco

[11] Patent Number: 5,445,822
[45] Date of Patent: Aug. 29, 1995

[54] COSMETIC COMPOSITIONS CONTAINING FATTY ACID TRIGLYCERIDE MIXTURES

[75] Inventor: Umberto Bracco, Vevey, Switzerland

[73] Assignee: Nestec S.A., Vevey, Switzerland

[21] Appl. No.: 234,271

[22] Filed: Apr. 28, 1994

[51] Int. Cl.⁶ ............................................. A61K 7/00
[52] U.S. Cl. .................................. 424/401; 424/400; 424/64; 424/63; 424/59; 252/107
[58] Field of Search ............... 424/401, 400, 64, 63, 424/59; 252/107

[56] References Cited

U.S. PATENT DOCUMENTS

| | | | |
|---|---|---|---|
| 4,454,159 | 6/1984 | Musher | 424/69 |
| 4,526,793 | 7/1985 | Ingenbleek | 426/72 |
| 4,938,984 | 7/1990 | Traitler et al. | 426/580 |
| 4,970,235 | 11/1990 | Traitler et al. | 514/558 |
| 5,011,855 | 4/1991 | Traitler et al. | 514/844 |
| 5,258,179 | 11/1993 | Bracco et al. | 514/690 |

FOREIGN PATENT DOCUMENTS

89606/91  6/1992  Australia .

OTHER PUBLICATIONS

European Search Report for EP 93 10 7589

*Primary Examiner*—Thurman K. Page
*Assistant Examiner*—Pamela S. Webber
*Attorney, Agent, or Firm*—Vogt & O'Donnell

[57] ABSTRACT

A topical cosmetic composition contains a cosmetic carrier and a mixture of fatty acid triglycerides. The fatty acids of the triglycerides include 40% to 70% by weight oleic acid, 30% to 50% by weight polyunsaturated acids, 0.2% to 1.0% by weight gamma-linolenic, 1% to 5% by weight alpha-linolenic acid, and the ratio by weight of n-6 fatty acids to n-3 fatty acids with a degree of unsaturation of 3 or more in the triglycerides is 10:1 to 30:1.

13 Claims, No Drawings

COSMETIC COMPOSITIONS CONTAINING FATTY ACID TRIGLYCERIDE MIXTURES

BACKGROUND OF THE INVENTION

This invention relates to a lipidic composition intended for use in cosmetic preparations.

Lipids perform several functions in cosmetics, namely:

- at the epidermal level, as structural elements of cell membranes and as barrier elements for preventing the imperceptible loss of water and hence drying out and
- at the intradermal level, as producers of bioactive substances.

These bioactive substances, which are produced by enzymatic transformation of the essential fatty acids, are responsible for physiological responses affecting the skin, such as inflammation, hyperproliferation and the intercell exchange mechanisms at the membrane level. It is known that lipids, particularly phospholipids incorporating the essential fatty acids, are the principal constituents of the membranes and regulate their enzymatic activity, the intercell signal receptors (the secondary messengers) and the production of eicosanoids.

The problem addressed by the present invention was to provide a lipidic composition for topical application based on a combination of oils formulated to guarantee optimal structural qualities and optimal physiological performance with an optimum balance of active substances to avoid unbalanced metabolic charges at the tissue level, more particularly at the skin level.

French Patent 2,670,111, for example, describes a fatty composition for cosmetic products of which the triglycerides comprise a significant proportion of saturated fatty acids and a minor proportion of unsaturated fatty acids. Under these conditions, the unsaturated oils are in danger of partly dissolving in the final mixture and separating from insoluble (saturated) glycerides during the production, storage or application of the product. In addition, no account is taken of a balance between the active substances of the n-3 and n-6 families, the isomerism of the alpha-linolenic (n-3 family) and gamma-linolenic (n-6 family) fatty acids or the fact that they compete with enzymes of the lipoxygenase type which produce from these fatty acids active metabolites intervening, for example, in the pro-inflammation and anti-inflammation processes.

SUMMARY OF THE INVENTION

The lipidic composition according to the present invention is characterized in that the fatty acids of the triglycerides contain 40 to 70% by weight of oleic acid and 30 to 50% by weight of polyunsaturated fatty acids, in that the ratio by weight of the fatty acids of the n-6 family to those of the n-3 family is 10:1 to 30:1 and in that the polyunsaturated fatty acids contain an effective quantity of acids of the n-3 and n-6 families with a degree of unsaturation of 3 or more.

The lipidic composition for topical application according to the present invention takes into account not only the activities of the essential fatty acids, but also the interaction of each essential fatty acid of the n-6 family, for example linoleic acid, with its homolog of the n-3 family, for example alpha-linolenic acid, the inability to the skin to convert these acids into higher unsaturated C 20 derivatives due to its lack of enzymatic capacity to desaturate the acids and the lipoxygenase activity of the skin and the reactivity of the hydroxy-acids produced by that activity.

DETAILED DESCRIPTION OF THE INVENTION

The composition of the present invention contains an oil rich in oleic acid which has an effect in terms of structure and as a vehicle on the essential bioactive fatty acids while being neutral from the point of view of bioactivity. The high oleic acid content provides the lipid mixture with high stability to oxidation and to photo-oxidation which avoids the formation of active oxygenated radicals.

The oils of choice which satisfy this requirement are preferably olive oil, hybrids of sunflower and safflower with a high oleic acid content, for example >70% weight. They also include the oleins of vegetable oils, for example palm oil, or animal oils, for example lard oil or tallow, obtained by dry, solvent or surfactant fractionation of oils and vegetable or animal oils and fats.

The oil in question makes up from 40 to 70% by weight, for example around 60% by weight, of the final lipid mixture.

The composition contains oils supplying the essential fatty acids belonging to the n-6 and n-3 families in a ratio which takes into account the greater reactivity of those of the n-3 family.

The oils rich in fatty acids of the n-6 family are selected from those rich in linoleic acid, preferably containing more than 65% by weight of that acid in relation to the total fatty acids, for example sunflower oil or grapeseed oil. Among these oils, the composition contains those which are capable of providing an effective quantity of acid with a degree of unsaturation of at least 3, for example gamma-linolenic acid, of which the function is to compensate the absence of desaturases from the skin. The oils in question include evening primrose oil, borage oil and, preferably, blackcurrant seed oil.

Oils supplying the fatty acids of the n-3 family include those which preferably contain more than 35% by weight of alpha-linolenic acid based on the total fatty acid, for example chia oil, linseed oil or, preferably, rosa mosqueta oil.

These "active" fatty acids may also be incorporated in the formulation in the form of free fatty acids and/or their esters with primary alcohols in quantities calculated to obtain the desired levels and relative proportions.

The mean fatty acid composition of the triglycerides of the final composition is as follows:

| Fatty acid | % by weight | | % by weight |
|---|---|---|---|
| C16:0 | 3–8 | preferably | 5 |
| C18:0 | 2–6 | preferably | 4 |
| C18:1 | 45–60 | preferably | 50 |
| C18:2 | 25–45 | preferably | 36 |
| C18:3, n-6 (gamma) | 0.2–1 | preferably | 0.5 |
| C18:3, n-3 (alpha) | 1–5 | preferably | 3.4 |
| C18:4, n-3 | 0.1–0.5 | preferably | 0.1 |
| >C20 | 1–3 | preferably | 1 |

On the basis of their respective fatty acid compositions, mixtures of the following oils are preferred:

| Oil | % by weight | | % by weight |
|---|---|---|---|
| Hybrid sunflower or safflower oil | 50–70 | preferably | 60 |

-continued

| Oil | % by weight | | % by weight |
|---|---|---|---|
| rich in oleic acid, Sunflower oil or grapeseed oil | 20–40 | preferably | 31 |
| Rosa mosqueta oil, chia oil or linseed oil | 3–10 | preferably | 6 |
| Blackcurrant seed oil | 1–10 | preferably | 3 |

To compensate a possible deficiency in the oil mixture of C20 fatty acids belonging to the n-3 family, the mixture may be enriched, for example, with the ethyl ester of eicosapentaenoic acid in a sufficient quantity, for example in a quantity of approximately 0.3% by weight.

The composition according to the invention may even contain other oils in minor quantities, for example to improve its keeping properties, for example a cereal germ oil rich in vitamin E as an antioxidant, or its organoleptic properties, for example apricot oil.

It may also contain fat-soluble or fat-solubilized antioxidants, for example a mixture of ascorbic acid, lecithin, tocopherol and vitamin B.

The lipidic composition according to the invention is advantageously used in various water-based or water-free cosmetic skin-care preparations, more particularly in water-based preparations, such as fluids, creams and milks for the face, the hands and the body, anti-sun creams and milks, anti-wrinkle creams and milks and similar preparations.

The cosmetic preparation in question may be formulated in particular as a solution, water-in-oil or oil-in-water emulsion, suspension or aerosol.

Water-free cosmetic preparations containing the lipidic composition according to the invention include oils for the body, water-free balms, anti-sun oils and lipsticks.

The lipidic composition according to the invention may make up from 1 to 80% by weight and preferably from 5 to 60% by weight of cosmetic preparations such as these.

Cosmetic preparations of the type in question generally contain suitable quantities of such additives as, for example, emulsifiers, antiperspirants, stabilizers, preservatives, UV filters, perfumes, colourants or emollients, waxes, pearlescers, mineral or organic fillers.

EXAMPLES

The invention is illustrated by the following Examples in which parts and percentages are by weight, unless otherwise indicated.

Example 1

The following refined oils in the proportions indicated are mixed with stirring under nitrogen.

| Oil | % |
|---|---|
| Hybrid sunflower oil containing 80% by weight of oleic acid, based on the fatty acids | 60 |
| Sunflower oil | 31 |
| Rosa mosqueta oil | 6 |
| Blackcurrant seed oil | 3 |

To this end, the blackcurrant seed oil and the rosa mosqueta oil are added to the hybrid and standard sunflower oils in a stainless steel reactor equipped with a double jacket system for the circulation of temperature control fluids and with a variable speed stirrer, temperatures above 30° C. being avoided. An antioxidant, for example vitamin E (tocopherol and its esters) or antioxidants of the phenolic type (for example butylhydroxyanisole) or natural extracts with an antioxidant effect (for example spices), is/are added to the mixture in quantities of up to 1,000 ppm (parts per million), based on the oil mixture. In a closed circuit, the mixture is packed in laminated-surface drums, preferably with a capacity of 25 kg, in a nitrogen atmosphere to avoid the oxidative degradations associated with the unsaturation of the mixture.

Example 2

The oil mixture is prepared as described in Example 1, A long-chain n-3 fatty acid is then added in concentrated form to provide the mixture with an optimal metabolism on the skin, taking into account any enzyme deficiencies present, for example, in the case of ageing and drying of the skin. The mixture contains the proportions indicated.

| Oil | % |
|---|---|
| Hybrid sunflower oil containing 80% by weight of oleic acid, based on the fatty acids | 60 |
| Sunflower oil | 31 |
| Rosa mosqueta oil | 5.7 |
| Blackcurrant seed oil | 3 |
| Eicosapentaenoic acid ethyl ester | 0.3 |

Example 3

| Ingredient | % |
|---|---|
| Propylene glycol | 2 |
| PEG 400 | 3 |
| Preservative | 0.3 |
| Carbopol 980 | 0.2 |
| Isopropyl myristate | 1 |
| Cetyl alcohol and stearic acid | 3 |
| Glycerol monostearate | 3 |
| Corn germ oil | 2 |
| Lipidic composition of Example 1 | 5 |
| Perfume | 0.5 |
| Demineralized water qsf | 100 |

This oil-in-water emulsion is prepared as follows: using a suitable homogenizer, the oily phase containing the lipidic composition of Example 1 containing other lipidic components and the emulsifiers of the formulation are homogenized in liquid phase in the aqueous phase consisting of demineralized water and the other hydrophilic components, such as preservatives, perfumes, etc.

Example 4

Body oil (anhydrous)

| Ingredients | % |
|---|---|
| Lipidic composition of Example 1 | 60 |
| Volatile silicone 7158 | 34.5 |
| Perfume | 0.5 |

Example 5

Oil-in-water emulsion

| Ingredients | % |
| --- | --- |
| Volatile silicone | 10 |
| Perhydrosqualene | 18 |
| Vaseline oil | 5 |
| Liquid lanolin | 4 |
| VASELINE | |
| Arlacel 165 (Atlas) | 6 |
| ARLACEL | |
| Tween 60 (Atlas) | 2 |
| TWEEN | |
| Cetyl alcohol | 1.2 |
| Stearic acid | 2.5 |
| Triethanolamine | 0.1 |
| Preservative | 0.3 |
| Antioxidants | 0.3 |
| Lipidic composition of Example 1 | 10 |
| Water qsf | 100 |

The lipidic components of the formulation are dissolved at 170° C. in the lipidic composition of Example 1. After addition of the emulsifiers ARLACEL 165 and TWEEN 60, the preservative and the antioxidant, this oily phase is emulsified by homogenization in the aqueous phase which forms the continuous phase of the emulsion. The emulsion is then cooled to ambient temperature and packed in containers.

Example 6

Water-in-oil emulsion

| Ingredients | % |
| --- | --- |
| PROTEGIN | 20 |
| VASELINE oil | 5 |
| Glycerine | 5 |
| Magnesium sulfate | 0.5 |
| Lipidic composition of Example 1 | 25 |
| Aromatic composition | 1 |
| Preservative | 0.3 |
| Water qsf | 100 |

The lipidic composition of Example 1 containing vaseline oil and PROTEGIN X forms the continuous phase of the emulsion obtained by adding the aqueous phase containing the glycerine and the magnesium salt to the lipidic phase at approximately 70° C. After addition of the aromatic composition and the preservative of the formulation, the emulsion is homogenized, cooled and packed in containers.

Example 7

Lipstick (anhydrous)

| Ingredients | % |
| --- | --- |
| Lipidic composition of Example 1 | 20 |
| Sesame oil | 9 |
| Castor oil | 15 |
| VASELINE oil | 15 |
| Lanolin | 15 |
| Beeswax | 5 |
| Ozocerite | 10 |
| Butylhydroxytoluene | 0.1 |
| Colourants | 5.9 |
| Titanium oxide | 5 |
| Perfume | qs |

The above anhydrous product is obtained in the same way as in Example 6 without homogenization by hot mixing and gradual cooling with slow stirring.

I claim:

1. A topical cosmetic composition contains a cosmetic carrier and a mixture of fatty acid triglycerides, wherein the fatty acids of the triglycerides comprise 40% to 70% by weight oleic acid, 30% to 50% by weight polyunsaturated acids, 0.2% to 1.0% by weight gamma-linolenic acid, 1% to 5% by weight alpha-linolenic acid, and wherein the ratio by weight of n-6 fatty acids to n-3 fatty acids with a degree of unsaturation of 3 or more in the triglycerides is 10:1 to 30:1.

2. A cosmetic composition according to claim 1 wherein the fatty acids of the triglycerides comprise 3% to 8% by weight palmitic acid, 2% to 6% stearic acid, 45% to 60% oleic acid, 25% to 45% linoleic acid, 0.1% to 0.5% stearidonic acid and 1% to 3% $>C_{20}$ fatty acids.

3. A cosmetic composition according to claim 1 wherein the triglyceride mixture comprises 50% to 70% by weight hybrid sunflower or safflower oil with a high oleic acid content; 20% to 40% by weight sunflower oil or grapeseed oil; 3% to 10% by weight rosa mosqueta oil, chia oil or linseed oil; and 1% to 10% by weight blackcurrant seed oil.

4. A cosmetic composition according to claim 1, 2 or 3 wherein the triglyceride mixture is present in the cosmetic composition in an amount of from 1% to 80% by weight, based upon the weight of the cosmetic composition.

5. A cosmetic composition according to claim 1, 2 or 3 wherein the triglyceride mixture is present in the cosmetic composition in an amount of from 5% to 60% by weight, based upon the weight of the cosmetic composition.

6. A cosmetic composition according to claim 1 in the form of a water-in-oil emulsion.

7. A cosmetic composition according to claim 1 in the form of an oil-in-water emulsion.

8. A cosmetic composition according to claim 1 in the form of a solution.

9. A cosmetic composition according to claim 1 in the form of a suspension.

10. A cosmetic composition according to claim 1 in the form of an aerosol.

11. A cosmetic composition according to claim 1 in the form of an anhydrous composition.

12. An anhydrous cosmetic composition according to claim 11 in the form of a lipstick.

13. A cosmetic composition according to claim 1 further comprising at least one member of the group consisting of emulsifiers, antiperspirants, stabilizers, preservatives, antioxidants, UV filters, perfumes, colorants, emollients, pearlescers, waxes, organic fillers and mineral fillers.

* * * * *

UNITED STATES PATENT AND TRADEMARK OFFICE
CERTIFICATE OF CORRECTION

PATENT NO. : 5,445,822
DATED : August 29, 1995
INVENTOR(S) : Umberto Bracco

It is certified that error appears in the above-indentified patent and that said Letters Patent is hereby corrected as shown below:

Title page, insert the following;

[30] Foreign Application Priority Data

May 10, 1993 [EP] European Pat. Off. ...93 107589.9

May 19, 1993 [EP] European Pat. Off. ...93 108201.0

Column 4, line 17, change the comma after "1" to a period.

Column 4, line 36, insert --Fluid (oil-in-water emulsion)--.

Signed and Sealed this

Thirty-first Day of October 1995

Attest:

BRUCE LEHMAN

*Attesting Officer*      *Commissioner of Patents and Trademarks*